US010595797B2

(12) United States Patent
Pascal et al.

(10) Patent No.: US 10,595,797 B2
(45) Date of Patent: Mar. 24, 2020

(54) DENTAL INTRAORAL RADIOLOGICAL IMAGE SENSOR

(71) Applicant: E2V SEMICONDUCTORS, Saint Egreve (FR)

(72) Inventors: Nathalie Pascal, Le Sappey-en-Chartreuse (FR); David Perennez, Grenoble (FR)

(73) Assignee: TELEDYNE E2V SEMICONDUCTORS SAS, Saint-Égrève (FR)

( * ) Notice: Subject to any disclaimer, the term of this patent is extended or adjusted under 35 U.S.C. 154(b) by 381 days.

(21) Appl. No.: 15/420,907

(22) Filed: Jan. 31, 2017

(65) Prior Publication Data
US 2018/0214096 A1 Aug. 2, 2018

(51) Int. Cl.
*A61B 6/14* (2006.01)
*A61B 5/00* (2006.01)
(Continued)

(52) U.S. Cl.
CPC ............ *A61B 6/145* (2013.01); *A61B 5/4547* (2013.01); *A61B 6/14* (2013.01); *G01T 1/244* (2013.01);
(Continued)

(58) Field of Classification Search
CPC ..... A61B 50/00; A61B 50/002; A61B 50/005; A61B 50/0066; A61B 50/0067; A61B 2560/00; A61B 2560/04; A61B 2560/0406; A61B 2560/0412; A61B 2562/00; A61B 2562/16; A61B 2562/17; A61B 2562/18;
(Continued)

(56) References Cited

U.S. PATENT DOCUMENTS

| 5,331,166 A | * | 7/1994 | Crosetto | A61B 6/145 |
| | | | | 250/368 |
| 6,169,781 B1 | * | 1/2001 | Doebert | A61B 6/145 |
| | | | | 378/189 |

(Continued)

FOREIGN PATENT DOCUMENTS

EP   003467109-0001   11/2016

OTHER PUBLICATIONS

Design U.S. Appl. No. 29/584,965, filed Nov. 18, 2016.
(Continued)

*Primary Examiner* — Anastasia Midkiff
(74) *Attorney, Agent, or Firm* — Pilloff Passino & Cosenza LLP; Sean A. Passino; Rachel K. Pilloff

(57) ABSTRACT

An intra-oral dental radiological image sensor is mechanically reinforced by two front $R_A$ and rear $R_B$ mechanical reinforcing plates each inserted between a respective face of an image capture module and a respective front 20A and rear 20B shell bottom of a casing. The front reinforcing plate is a solid plate, made of material transparent to X rays, covering the photosensitive front face (scintillator) of the module, and harder than the front shell. The rear plate, less thick than the front plate, is harder than the rear shell and comprises an opening O provided to surround, without covering them, components present on the rear face of the module, under a rear shell dome.

20 Claims, 3 Drawing Sheets

(51) Int. Cl.
*H01L 27/146* (2006.01)
*H01L 27/148* (2006.01)
*G01T 1/24* (2006.01)
*G03B 42/04* (2006.01)

(52) U.S. Cl.
CPC ...... *G03B 42/042* (2013.01); *H01L 27/14601* (2013.01); *H01L 27/14806* (2013.01); *A61B 2560/0412* (2013.01); *A61B 2562/17* (2017.08); *A61B 2562/18* (2013.01); *A61B 2562/227* (2013.01)

(58) Field of Classification Search
CPC .......... A61B 2562/185; A61B 2562/22; A61B 2562/221; A61B 2562/222; A61B 2562/225; A61B 2562/227; A61B 5/00; A61B 5/45; A61B 5/4538; A61B 5/4542; A61B 5/4547; A61B 6/00; A61B 6/06; A61B 6/10; A61B 6/107; A61B 6/14; A61B 6/145; A61B 6/42; A61B 6/4208; A61B 6/425; A61B 6/4283; A61B 6/50; A61B 6/501; H01L 27/14; H01L 27/144; H01L 27/146; H01L 27/14601; H01L 27/14658; H01L 27/14676; H01L 27/14683; H01L 27/1469; H01L 27/148; H01L 27/14806; H01L 27/14831; H01L 27/14893; G01T 1/243; G01T 1/244; G03B 42/00; G03B 42/02; G03B 42/04; G03B 42/042

See application file for complete search history.

(56) References Cited

U.S. PATENT DOCUMENTS

| | | | | |
|---|---|---|---|---|
| 6,527,442 | B2* | 3/2003 | Carroll | A61B 6/14 348/E3.02 |
| 6,652,141 | B1* | 11/2003 | Cianciosi | A61B 6/145 378/191 |
| 7,866,163 | B2* | 1/2011 | Ertel | G01T 1/2928 62/3.2 |
| 7,972,060 | B2 | 7/2011 | Guichard et al. | |
| 8,366,318 | B2* | 2/2013 | Zeller | A61B 6/145 378/168 |
| 2004/0238721 | A1* | 12/2004 | Miyaguchi | A61B 6/4233 250/208.1 |
| 2013/0129044 | A1* | 5/2013 | Yoon | A61B 6/145 378/62 |
| 2016/0038104 | A1 | 2/2016 | Heo et al. | |
| 2016/0135763 | A1 | 5/2016 | Zeller et al. | |

OTHER PUBLICATIONS

RO101 for PCT/EP2017/053047, filed Feb. 10, 2017.
International Search Report and Written Opinion for PCT/EP2017/053047, dated Oct. 19, 2017.

\* cited by examiner

PRIOR ART

DENTAL INTRAORAL RADIOLOGICAL IMAGE SENSOR

FIELD

The invention relates to an intra-oral dental radiological sensor, and more specifically to a construction of such a sensor, which is better suited to use not only in the human medical field but also, and above all, in the veterinary field.

STATE OF THE ART

An intra-oral dental radiological sensor is a sensor which comprises an electronic image capture module enclosed in a casing, whose form closely follows that of the module, to meet a need for compactness in accordance with the intended use of the product. Generally, a link cable is provided which makes it possible to connect the sensor to an operating system for the images which are collected and which also serves to manipulate the sensor, facilitating the positioning thereof in the buccal cavity.

The electronic module consists of a stack of flat elements, forming a generally rectangular parallelepiped (possibly with cut corners), not very thick, whose surface dimensions are dictated by those of the images to be taken: at least the height of a tooth and of the bottom gum in the widthwise direction of the rectangular module and of the casing and the width of several teeth in the lengthwise direction of the module and of the casing.

The module comprises at least one electronic chip (CMOS, CCD), a scintillator covering the front face of the chip, and a printed circuit board whose front face supports the rear face of the chip. A spool of optical fibres is sometimes inserted between the chip and the scintillator. The chip is the imaging element of the sensor and comprises a matrix of photosensitive elements and associated electronic circuits. The scintillator forms the front face of the module, to be exposed to the ionizing radiation to be detected (X or gamma). The rear face of the module corresponds to the rear face of the printed circuit board supporting the chip. This rear face of the module further has one or more discrete components, which allow the module to be interfaced with the outside. In the example of a connection by link cable, the rear face of the module, that is to say the rear face of the printed circuit board, thus comprises a link cable connection element, generally a connector to be connected to a corresponding connector of the link cable (but that could also be a set of conductive tracks to be connected by soldering to corresponding conductor wires of the link cable). The rear face of the module can comprise other components. For example, if the link cable is a cable according to the USB (Universal Serial Bus) standard, it is possible to place, on the rear face of the module, a USB connector and associated electronic components which ensure the interface between the input/output signals of the electronic chip and those of the USB connector. It is also possible to have, on the rear face of the module, a ground contact point linking the ground of the electronic chip and a ground of the printed circuit.

The casing has a form which closely follows the form of the module by taking into account the various components mounted on the rear face. It is formed by the assembly of a front shell with a flat bottom which covers the front face of the module, and a rear shell with a bottom that is partly flat but which has a dome protruding outwards, to enclose within the end of the link cable when such a cable is provided. The link cable passes through an opening of the dome; it is connected to the connector of the printed circuit of the module inside the dome; and it leaves the dome generally in a direction parallel to a large side of the module.

The construction and the assembly of the elements of the intra-oral dental radiological sensor meet various constraints associated with the use of the sensor: patient comfort, strength of the sensor and above all of the electronic chip and of the scintillator in case of impact due for example to being dropped, seal-tightness in use, seal-tightness and strength in a sterilization situation, resistance of the cable to being pulled out, etc. It is the role of the casing to ensure these functions, and, moreover, the casing has to be constructed, at least on its front face, from a material that is transparent to the X or gamma radiation used for the radiological imaging.

The module is sometimes jacketed with a thin sheet of aluminium (low radiation absorption), and the edges of the module are sometimes protected by wafers of elastic material as is described in the patent U.S. Pat. No. 7,972,060.

The sensors of the prior art are, however, difficult to use in usages where the risks of mechanical stresses are particularly severe, as in the case of veterinary use where it is not easy to control the pressure exerted by the jaws of the animal on the sensor. In effect, it is not possible to ask it to control this pressure during the dental examination, and, moreover, when subjected to anaesthesia for this examination, it may keep the jaws strongly clamped at rest.

The professionals involved therefore need intra-oral sensors that are compact but capable of operating in the presence of more severe usage constraints, so as to have a reasonable life span in veterinary conditions of use.

SUMMARY

The invention thus proposes an intra-oral dental radiological sensor construction comprising an electronic imaging module, of generally rectangular form, possibly with cut corners, comprising, on a photosensitive front face, an electronic imaging chip covered with a scintillator, and, on a rear face, components including a connector for linking the module to a link cable, the module being contained in a protective casing formed by a flat-bottomed front shell and a rear shell having a bottom that is partly flat and a protruding dome which covers at least the connector and, possibly, other components protruding on the rear face of the module. The sensor further comprises a front mechanical reinforcing plate, which is a solid plate, inserted between the flat bottom of the front shell and the front face of the electronic module, the front reinforcing plate having a hardness greater than that of the front shell and being transparent to X rays;

a rear mechanical reinforcing plate, less thick than the front reinforcing plate, inserted between the flat bottom of the rear shell and the rear face (30b) of the electronic module, and open so as to surround, without covering them, at least the link connector and said other protruding components, the rear reinforcing plate having a hardness greater than that of the rear shell.

Since the reinforcing plates are inside the casing, the material used for these plates does not have to meet the same constraints as the material of the casing, notably the constraints concerning seal-tightness in use and in sterilization, which makes it possible to consider materials that are more efficient in terms of hardness and rigidity than those of the casing. It is thus possible to produce mechanical reinforcing plates that are less thick than the material of the casing, which makes it possible to obtain a reinforced mechanical protection without significantly affecting the outer dimensions of the casing.

The two reinforcing plates are defined with a hardness and a rigidity that are preferably equivalent, but the front plate is thicker than the rear plate. They are also defined with different forms, the front plate being solid and the rear plate being in the form of a closed or partially open frame, surrounding the components protruding on the rear face of the module and notably the connector which allows for the link with a transmission cable when a cable link is provided.

The invention will be better understood from the following detailed description taken in conjunction with the attached drawings.

DETAILED DESCRIPTION

The invention will be described by way of example with respect to a flat intra-oral radiological image sensor which is equipped with a link cable, for the transmission of the radio image data to an external display system. However, the invention would apply similarly to a sensor with wireless transmission.

First, it should be noted that the figures are not to scale. In particular, the thickness of the casing of the sensor, on the axis z at right angles to the front and rear faces of the casing, is in reality smaller than that which is represented.

Figure 1:
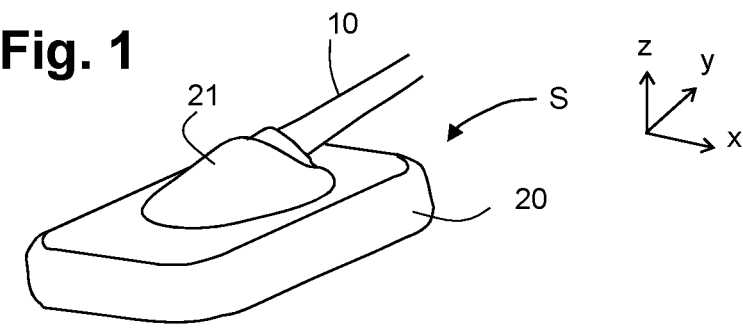
FIG. 1 represents a general view of an intra-oral radiological sensor according to the prior art.

The casing 20 of the sensor S of FIG. 1 comprises a front face intended to be exposed to the X rays and a rear face opposite the front face.

Figure 2:
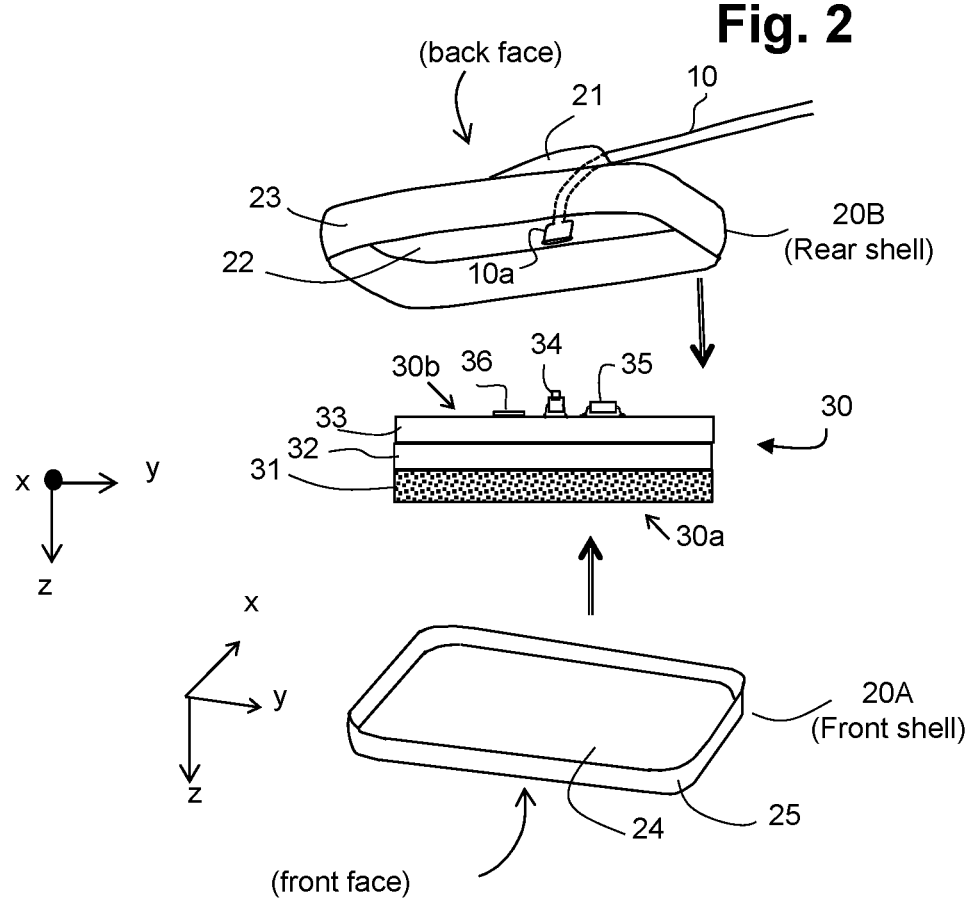
FIG. 2 illustrates the elements and the steps of assembly of this sensor.

FIG. 1 is, more specifically, a view of the sensor S from the rear face, which comprises a protruding dome 21 from which the link cable 10 exits making it possible to connect the sensor to an operating and display system for the images collected. The cable exits parallel, or almost parallel, to the plane of the rear face of the casing 20. The front face of the sensor which is not visible in this figure is that which has to be exposed to the radiation to be detected. FIG. 2 details the constituent elements of the sensor: a casing 20 formed by the assembly of a front face shell 20A and of a rear face shell 20B and closely following the form of an electronic imaging module 30 enclosed between the two shells.

The imaging module comprises a photosensitive front face intended to be exposed to the X rays, and hereinbelow the front face of a flat element of the sensor will describe the surface which is situated on the same side as the photosensitive face of the electronic module. The rear face denotes the opposite face.

The module 30 is a stack of flat elements comprising, from the rear face 30b of the module to the front face 30a of the module, a printed circuit board 33, an electronic matrix imaging chip 32, which can be a CMOS or CCD integrated circuit, and a scintillator 31 covering the photosensitive front face of the chip, in that order. In some cases, an optical transmission layer (fibre optics) is provided between the chip and the scintillator (not represented).

The rear face 30b of the module is the rear face of the printed circuit board 33, and it supports one or more discrete components. In the case of a sensor provided with a link cable for interfacing the sensor with an image display system, these components comprise at least one connector 34, provided to be connected to the corresponding connector 10a mounted on an end of the link cable 10 (it is of course possible to make the connection in another way, by soldering the stripped ends of the conductor wires of the link cable onto corresponding conductive tracks provided on the rear face of the printed circuit. The term "connector" as used in the present application combines these different, fixed or removable, connection configurations).

One or more other components 35 can be provided on the rear face 30b. That may be the case in particular when the link cable is a cable of USB type, making it possible to directly connect the sensor as a USB peripheral of a computer: the matching of the input/output signals of the imaging chip to the USB bus is then done in the electronic module by these discrete components. Also, a metallic ground contact zone 36 can be provided to link the common ground of the printed circuit to a common ground of the electronic chip.

Thus, therefore, the electronic module 30 usually comes with a front face (of scintillator 31) which is completely flat, and a rear face (of printed circuit 33), which is not flat or not completely flat because it supports one or more components 34, 35, 36 grouped together in a delimited zone of this rear face.

The electronic module is mounted in the casing 20 formed by a rear shell and a front shell. The two shells 20A and 20B are produced in a hard material (generally plastic, composite resin, or metal), and the material of the front shell at least is permeable to the radiation to be detected (X rays), that is to say that it induces very little in the way of absorption losses.

The rear shell 20B is formed by a bottom 22 edged over its entire perimeter by a rim 23 (lateral peripheral wall). The bottom 22 comprises an outwardly protruding dome 21 from which the link cable 10 exits, through an opening formed in the dome. One end of the link cable is located inside the dome, and it is provided, in the example, with a connector 10a to be connected to the connector 34 present on the printed circuit of the rear face of the module.

The front shell 20A comprises a flat bottom 24. In the example, it can also comprise a slight rim 25 over its perimeter as illustrated. However, it could also be a simple closure plate, the depth of the casing then being essentially given by the height of the lateral peripheral wall of the rear shell.

The module and the front and rear shells of the casing are usually assembled as follows:
the module is arranged with the rear face 30b turned towards the bottom of the rear shell 20B which is oriented in such a way that the link cable exits from the dome parallel or almost parallel to the surface plane of the module, and in a direction generally parallel to a large side of the rectangular module;

the connector 10a of the link cable is connected to the connector 34 of the electronic module; then, the connected module is pushed against the bottom 22 of the rear shell; the interconnected connectors 34 and 10a, any other rear face components 35 (primarily those which protrude from the rear face plane of the printed circuit) and the part of link cable 10 inside the casing are contained under the dome 21 of the rear shell;

the front shell 20A is added on top of the front face of the module, the flat bottom of this front shell covering the front face (scintillator) of the module, and coming to bear against the lateral peripheral walls of the rear shell;

the front and rear shells are glued or welded to one another by their edges by any known technique.

The link cable usually exits along the longitudinal axis of the module (along the axis y) in the plane of the sensor. That simplifies the placement and the holding of the sensor in vertical position in the buccal cavity: the width of the sensor (small side) corresponds to an image height covering a tooth height, and the length of the sensor (large side) corresponds to an image width covering one or more teeth.

Figure 3:
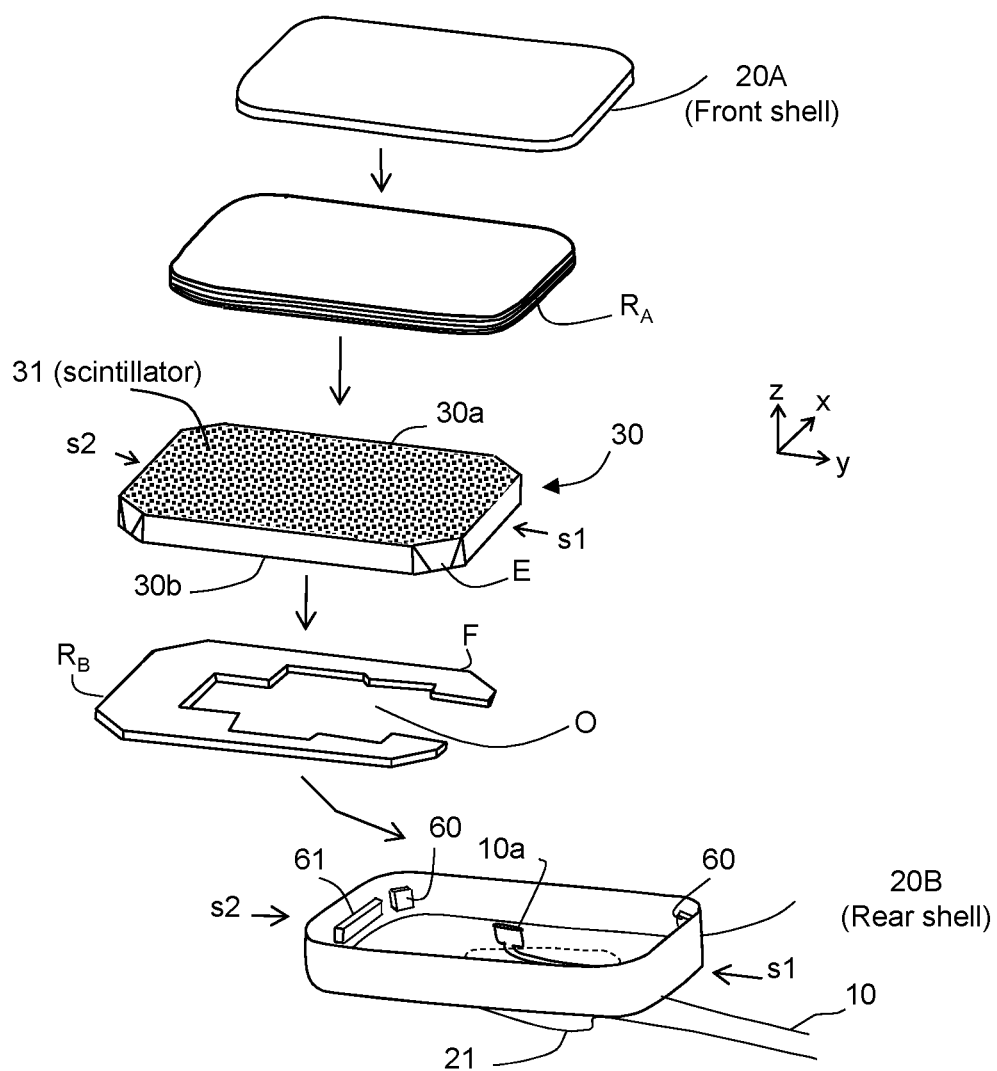
FIG. 3 illustrates a construction of an intra-oral radiological sensor according to the invention.
Figure 4:
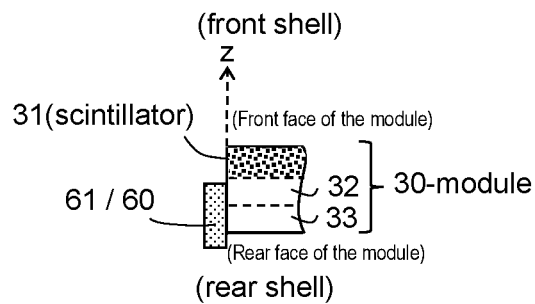
FIG. 4 is a partial cross section in a plane zy at right angles to the front and rear faces of the module, showing the heightwise position of the elastic damping elements in relation to the scintillator.
Figure 5:
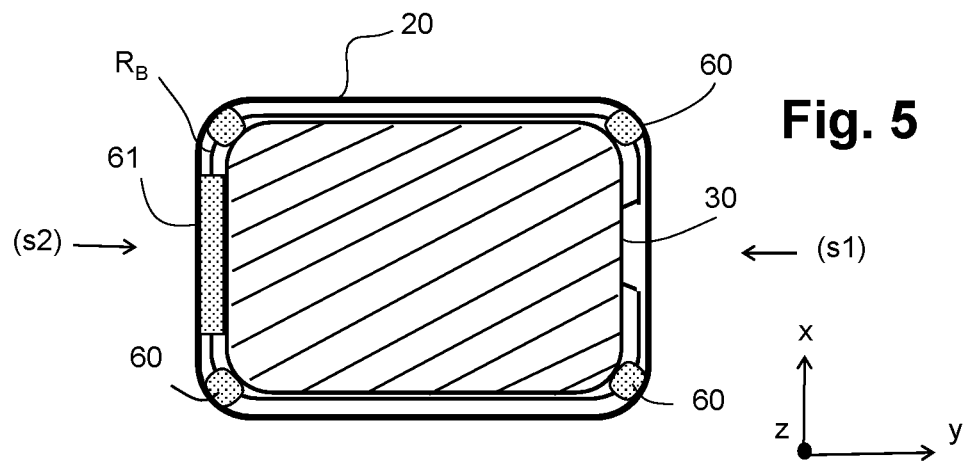
FIG. 5 is a plan view in a plane parallel to the front and rear faces of the module, showing the arrangement of the module inside the casing according to an embodiment of the invention.

FIGS. 3 to 5 illustrate a construction of a sensor according to the invention. It comprises, like that of FIGS. 1 and 2, an electronic imaging module 30 (electronic chip, scintillator, printed circuit and components) enclosed in a casing composed of two shells (20A, 20B), of which one has a dome through which a link cable exits (when a cable connection is provided). These elements, module and casing, will not be described again in detail hereinbelow and the same references as in FIGS. 1 and 2 will be used hereinbelow.

The sensor of FIGS. 3 to 5 further comprises two mechanical reinforcing plates, each inserted between one of the rear and front shell bottoms and the module.

The mechanical reinforcing plates are plates which have hardness and rigidity properties greater than those of the front and rear shells. The hardness of the plate defines the relative strength with which the surface opposes the penetration of a harder body, and it is determined for a given material by measuring the depth, the diameter or another parameter of the imprint made by a punch. The rigidity describes the degree of elastic deformation (the elongation) under a defined applied strain considered here in the direction of the thickness of the sensor.

The front reinforcing plate is transparent to the radiation to be detected and its constituent material is chosen accordingly. The rear reinforcing plate does not need to be transparent to the radiation which makes it possible to produce it in a material that is intrinsically harder and more rigid than that of the front plate since the materials are not limited to materials that are transparent to the radiation. The thickness of the rear reinforcing plate is less than that of the front reinforcing plate.

The front reinforcing plate $R_A$ (FIG. 3) is a solid plate covering all the surface of the scintillator; it is pressed against the front face of the module that it entirely covers. The surface area of the plate $R_A$ is thus at least equal to the surface area of the front face of the module. This front plate material can be a single-layer or multilayer polymer, a ceramic, or a metal (transparent to the X rays), but thick enough to be rigid, or even a single-layer or multilayer composite material. This material is preferably a composite having a multilayer structure allowing for increased rigidity, such as, for example, a composite of epoxy resin and cotton fabrics marketed under the trademark Tufnol (registered trademark), or a composite with multilayer structure offering equivalent hardness and rigidity properties for the geometry chosen (form, surface area, thickness) for the front plate.

The rear reinforcing plate $R_B$ is a plate in the form of a frame, which is pressed against the rear face of the module, between this rear face and the rear shell bottom. The frame surrounds an opening O into which those components of the printed circuit which protrude on the rear face of the printed circuit, and notably the connector 34 of the link cable, can pass. Thus, the presence of the reinforcing plate against the rear face of the module remains possible despite the presence of these protruding components.

The frame is closed around the opening O, or partially open (therefore in the general form of a U) around this opening. In FIG. 3, the frame is partially open on the right side. The U-shaped open form of the frame simplifies the placement of the assembly of the elements of the sensor before the two shells are welded. The rear reinforcing plate can be put in place against the rear shell bottom, by sliding in the longitudinal direction towards the link cable exit side, naturally bringing the link cable into the frame opening, with no particular manipulation, simplifying the positioning and the pressing of the plate against the rear face of the module, with the discrete components and the connection to the link cable contained inside the frame opening and under the rear shell dome.

The material of the rear reinforcing plate can be a single-layer or multilayer polymer, a ceramic or a metal, or a composite material. It is preferably a reinforced polymer composite, for example reinforced by long carbon fibres, for example a polyphthalamide reinforced with long carbon fibres such as the material PPA CF30 (standardized designation), or a material offering equivalent hardness and rigidity properties for this geometry (form, surface area, thickness) of the rear plate.

Preferably, the front and rear plate materials and thicknesses are determined in practice to obtain a hardness and a rigidity that are equivalent for the two plates, to offer one and the same bite resistance on both sides.

In an example, the thickness of the front reinforcing plate will be in a ratio of 2.5 to 5% of the plate length, for example 2 millimetres for a length of 40 millimetres for a ratio of 5%, and that of the rear reinforcing plate will be in a ratio of 1 to 1.5% of the plate length, for example 0.6 millimetre for a length of 40 millimetres, fora ratio of 1.5%.

The inclusion of the two reinforcing plates, in optimized geometries and materials, makes it possible to notably improve the resistance to impacts exerted head-on on the front and/or the rear of the sensor, especially to bites, without significantly affecting the compactness.

In the open zone of the frame, the rear face surface of the module is protected by the combined effect of protection provided by the presence, above this zone, of the dome and of the cable. This dome plus cable assembly acts both as spacer and as damper with respect to this rear face zone in the open zone of the frame.

Figure 6:
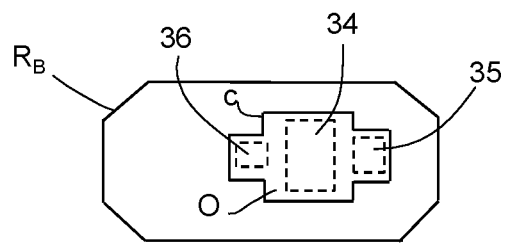
FIG. 6 is a plan view of the rear reinforcing plate, in a closed frame, cut so as to surround the protruding components.

In a variant represented in FIG. 6, the plate frame is closed around the opening O and the link cable has to be passed through the plate opening O to connect it to the connector 34.

In both open and closed frame configurations of the rear reinforcing plate, the outline c (FIG. 6) of the plate opening O is preferably such that it outlines as closely as possible all the components (34 to 36 in the example) which protrude on the rear face of the printed circuit 33 so as to obtain the greatest possible contact surface area between the rear plate frame $R_B$ and the rear face of the module, for an optimal protection. In other words, the rear face surface area directly protected by the rear reinforcing plate is as large as possible.

According to another aspect of the invention illustrated in FIGS. 3 to 5, elastic separator elements 60, 61 are provided between the module and the inner peripheral wall of the casing to protect the module effectively against lateral impacts (that are exerted against the edge of the stack of the module). In the example, these elastic elements are glued onto the inner lateral peripheral wall of the rear shell. An elastic separator element 60 is thus provided, in the form of a small cube, arranged facing each corner of the module. The corners of the sensor are in fact parts that are highly exposed to impacts when being manipulated. The four elements 60 further simplify the positioning and the holding of the module when being mounted in the rear shell.

Advantageously, a slender elastic separator element 61 is provided to at least protect the small side (s2) of the module which is opposite the link cable exit side (s1). This element 61 provides mechanical protection to lateral impacts on this side (s2) of the sensor, which is the side most exposed to mechanical impacts (lateral impacts, drops). In effect, on the other small side s1, the presence of the link cable reduces the occurrence of impacts and practice shows that the two large sides of the module, which are in the same direction as the cable and correspond to the image width, are generally less exposed.

Thus, by providing the slender elastic element on just this small side s2, rather than on both the small sides of the module, there is a gain in compactness, without degrading the protection of the module against lateral impacts.

These elastic separator elements 60 and 61 are produced in an elastic and resilient material, that is to say a material having a high capacity for absorbing energy when it is deformed under the effect of an impact (rapid deformation). For example, and in a nonlimiting manner, a material will be used from the following list of materials: natural rubber (NR), polybutadiene rubber (BR), or styrene butadiene rubber (SBR), or ethylene propylene diene monomer (EPDM), or nitride of rubber (NBR), etc. It is also possible to use a polyurethane (PUR).

In practice, these damping elements 60, 61 are added at the appropriate points by gluing, generally onto the inner peripheral wall of the casing (rear shell). The height of these elements in the direction of the thickness of the stack of the module (axis z) and their position are adjusted so that the top scintillator layer 31 remains wholly at a higher level than the elastic elements as can be seen in FIG. 4, to avoid any contact between the elastic elements and the scintillator which is particularly brittle. The damping elastic elements face the edge of the module over the rest of the height of this edge. The elements 60 and 61 thus act as lateral spacers with respect to the scintillator layer of the module relative to the internal periphery of the casing, protecting this layer from lateral impacts.

According to another aspect of the invention, provision is made for the front and/or rear reinforcing plate to slightly overhang the module in x and/or in y, within the limits of the thickness of the damping elements 60, 61. In other words, the overhang in x and/or in y of a plate (or of the outer outline of the plate) relative to the module surface on which the plate is arranged is less than the thickness of the damping elements. In this way, the benefit of a greater tolerance in the positioning of the plate relative to the module, for optimal protection, without degrading compactness, is obtained. For example, it can be seen in FIG. 5 that the rear reinforcing plate $R_B$, which appears under the module 30 and the damping elements 60 and 61, overhangs in y (that is to say on the small side or sides) relative to the module. This overhang is visible on the partial transverse cross-sectional view (because the rear and front shells are not shown therein, for simplification) of FIG. 5. The internal dimensions of the casing, and more specifically of the rear shell, are configured to correspond as closely as possible to the dimensions of the module and of the rear plates). An overhang of the plate in the direction x is possible but not necessary.

The assembly of the module, of the front and rear shells, and of the reinforcing plates will generally proceed as follows:

a—the rear reinforcing plate $R_B$ is placed against the bottom of the rear shell 20B provided with elastic separator elements 60 and 61 previously glued at the appropriate points, by sliding it on the open side of the frame towards the corresponding small side of the module so as to pass the link cable into the plate opening, as indicated in FIG. 3;

b—the rear face connector 34 of the module 30 is connected to the connector 10a of the link cable, and the connected module is pushed against the rear reinforcing plate, by containing the connector 34 connected to the link cable and any other rear face components 35 in the space delimited by the rear shell dome 21 and the plate opening O;

c—the front reinforcing plate $R_A$ is added on top of the front face of the module;

d—the front shell 20A is added on top of the front reinforcing plate $R_A$, edge-to-edge with the rear shell;

e—the front and rear shells are glued or welded to one another by their edges by any usual technique.

Preferably, before the step a), provision is made to jacket the module (except for the rear face part comprising the components) in a protective sheet E that is transparent to the radiation, typically a sheet of aluminium.

The invention claimed is:
1. An intra oral dental radiological image sensor comprising,
an electronic imaging module, comprising,
on a photosensitive front face, an electronic imaging chip covered with a scintillator, and,
on a rear face, components including a connector for linking the electronic imaging module to a link cable,
the electronic imaging module being contained in a protective casing formed by
a front shell having a flat bottom, and
a rear shell having a bottom that has a partly flat portion and a protruding dome which covers at least the connector, and
the sensor further comprising
a front mechanical reinforcing plate, which is a solid plate, between the flat bottom of the front shell and the photosensitive front face of the electronic imaging module, the front reinforcing plate having a hardness greater than that of the front shell and being transparent to X rays or gamma rays; and
a rear mechanical reinforcing plate, less thick than the front mechanical reinforcing plate, between the partially flat portion of the bottom of the rear shell and the rear face of the electronic imaging module, wherein the rear mechanical reinforcing plate is in the form of a frame having an opening into which the components including the connector protrude, the rear reinforcing plate having a hardness greater than that of the rear shell.

2. The sensor of claim 1, wherein the rear mechanical reinforcing plate is in the form of a U-shaped open frame, which is partially open around the opening of the frame.

3. The sensor of claim 1, wherein the protective casing has an inner wall, and the sensor further comprises at least one elastic separator element between the electronic imaging module and the inner wall of the protective casing.

4. The sensor of claim 3:
wherein a height axis (z) of the protective casing is perpendicular to a x-y plane defined by the flat bottom of the rear shell, and positively oriented from the flat bottom of the rear shell to the flat bottom of the front shell, and
wherein the elastic separator element is at a height level on the height axis (z) wholly below that of the scintillator, avoiding any contact between the elastic element and the scintillator.

5. The sensor of claim 3, wherein the rear mechanical reinforcing plate overhangs, relative to a line perpendicular to the x-y plane, the rear face of the electronic imaging module.

6. The sensor of claim 1, wherein the front mechanical reinforcing plate has a multilayer structure.

7. The sensor of claim 6, wherein the front mechanical reinforcing plate is a composite of epoxy resin and cotton fabrics.

8. The sensor of claim 1, wherein the rear mechanical reinforcing plate is a carbon fibre reinforced polymer composite.

9. The sensor of claim 2, wherein the protective casing has an inner wall, and the sensor further comprises at least one elastic separator element between the electronic imaging module and the inner wall of the protective casing.

10. The sensor of claim 9:
wherein a height (z) of the protective casing is perpendicular to a x-y plane defined by the flat bottom of the rear shell, and positively oriented from the flat bottom of the rear shell to the flat bottom of the front shell, and
wherein the elastic separator element is at a height level on the height axis (z) wholly below that of the scintillator, avoiding any contact between the elastic element and the scintillator.

11. The sensor of claim 9, wherein the rear mechanical reinforcing plate overhangs, relative to a line perpendicular to the x-y plane, the rear face of the electronic imaging module.

12. The sensor of claim 1, wherein the electronic imaging module has a rectangular form.

13. The sensor of claim 12, wherein the rectangular form has cut corners.

14. The sensor of claim 13, wherein the protective casing has an inner wall and corners, and the sensor further comprises an elastic separator element between each corner of the electronic imaging module and the protective casing.

15. The sensor of claim 12, wherein the protective casing has an inner wall and corners, and the sensor further comprises an elastic separator element between each corner of the electronic imaging module and the protective casing.

16. The sensor of claim 1, wherein the protruding dome further covers a component other than the connector.

17. The sensor of claim 1, wherein the frame is closed around the opening of the frame.

18. The sensor of claim 2, wherein the protruding dome has an opening to receive the link cable.

19. The sensor of claim 12, wherein the protruding dome has an opening to receive the link cable.

20. The sensor of claim 19, wherein the opening of the protruding dome is configured such that the link cable exits from the protruding dome a direction along a larger side of the rectangular electronic imaging module.

* * * * *